US011676703B2

(12) United States Patent
Vaidya et al.

(10) Patent No.: US 11,676,703 B2
(45) Date of Patent: Jun. 13, 2023

(54) COMBINATION OF RADIOMIC AND PATHOMIC FEATURES IN THE PREDICTION OF PROGNOSES FOR TUMORS

(71) Applicant: Case Western Reserve University, Cleveland, OH (US)

(72) Inventors: Pranjal Vaidya, Cleveland, OH (US); Anant Madabhushi, Shaker Heights, OH (US); Kaustav Bera, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 192 days.

(21) Appl. No.: 17/068,103

(22) Filed: Oct. 12, 2020

(65) Prior Publication Data
US 2021/0110541 A1 Apr. 15, 2021

Related U.S. Application Data

(60) Provisional application No. 62/913,900, filed on Oct. 11, 2019.

(51) Int. Cl.
*G16H 30/40* (2018.01)
*G06T 7/00* (2017.01)
(Continued)

(52) U.S. Cl.
CPC .......... *G16H 30/40* (2018.01); *G06F 18/214* (2023.01); *G06T 7/0012* (2013.01);
(Continued)

(58) Field of Classification Search
CPC ......... G06T 7/0012; G06T 2207/10072; G06T 2207/20081; G06T 2207/20084;
(Continued)

(56) References Cited

U.S. PATENT DOCUMENTS

2014/0233826 A1* 8/2014 Agaian ................ G06V 20/698
382/133
2014/0314292 A1* 10/2014 Kamen .................. G16H 30/20
435/29
(Continued)

OTHER PUBLICATIONS

Sorace et al. "Integrating pathology and radiology disciplines: an emerging opportunity?", BMC Medicine, 10:100, 2012 (Year: 2012).*
(Continued)

*Primary Examiner* — Vu Le
*Assistant Examiner* — Julius Chai
(74) *Attorney, Agent, or Firm* — Eschweiler & Potashnik, LLC (57) ABSTRACT

Embodiments discussed herein facilitate building and/or employing model(s) for determining tumor prognoses based on a combination of radiomic features and pathomic features. One example embodiment can perform actions comprising: providing, to a first machine learning model, at least one of: one or more intra-tumoral radiomic features associated with a tumor or one or more peri-tumoral radiomic features associated with a peri-tumoral region around the tumor; receiving a first predicted prognosis associated with the tumor from the first machine learning model; providing, to a second machine learning model, one or more pathomic features associated with the tumor; receiving a second predicted prognosis associated with the tumor from the second machine learning model; and generating a combined prognosis associated with the tumor based on the first predicted prognosis and the second predicted prognosis.

27 Claims, 3 Drawing Sheets

(51) Int. Cl.
*G16H 50/20* (2018.01)
*G06F 18/214* (2023.01)
*G06V 10/764* (2022.01)
*G06V 10/774* (2022.01)
*G06V 10/80* (2022.01)
*G06V 10/82* (2022.01)
*G06V 10/44* (2022.01)

(52) U.S. Cl.
CPC .......... *G06V 10/454* (2022.01); *G06V 10/764* (2022.01); *G06V 10/7747* (2022.01); *G06V 10/811* (2022.01); *G06V 10/82* (2022.01); *G16H 50/20* (2018.01); *G06T 2207/10072* (2013.01); *G06T 2207/20081* (2013.01); *G06T 2207/20084* (2013.01); *G06T 2207/30061* (2013.01); *G06T 2207/30096* (2013.01); *G06V 2201/03* (2022.01)

(58) Field of Classification Search
CPC .......... G06T 2207/30061; G06T 2207/30096; G16H 50/20; G16H 30/40; G06K 9/6256; G06V 2201/03
See application file for complete search history.

(56) References Cited

U.S. PATENT DOCUMENTS

| | | | |
|---|---|---|---|
| 2016/0196648 A1* | 7/2016 | Madabhushi | A61P 37/00 382/131 |
| 2016/0203599 A1* | 7/2016 | Gillies | A61B 5/7271 382/132 |
| 2017/0351939 A1* | 12/2017 | Madabhushi | G06K 9/6267 |
| 2018/0374583 A1* | 12/2018 | Goldstein | G06G 1/14 |
| 2019/0371450 A1* | 12/2019 | Lou | G16H 10/60 |
| 2020/0272864 A1* | 8/2020 | Faust | G06V 10/25 |
| 2021/0166785 A1* | 6/2021 | Yip | G16B 30/00 |
| 2021/0271847 A1* | 9/2021 | Courtiol | G06K 9/6218 |

OTHER PUBLICATIONS

Prasanna P et al., "Co-occurrence of Local Anisotropic Gradient Orientations (CoLIAGe): A new radiomics descriptor.", Sci Rep. Nov. 22, 2016;6:37241. doi: 10.1038/srep37241. PMID: 27872484; PMCID: PMC5118705. (Year: 2016).*

Shiradkar, Rakesh, et al. "Radiomic features from pretreatment biparametric MRI predict prostate cancer biochemical recurrence: preliminary findings." Journal of Magnetic Resonance Imaging 48.6 (2018): 1626-1636. (Year: 2018).*

* cited by examiner

COMBINATION OF RADIOMIC AND PATHOMIC FEATURES IN THE PREDICTION OF PROGNOSES FOR TUMORS

CROSS REFERENCE TO RELATED APPLICATIONS

This application claims the benefit of U.S. Provisional Patent Application No. 62/913,900 filed Oct. 11, 2019, entitled "COMBINATION OF RADIOMIC AND PATHOMIC SIGNATURE IN THE NOMOGRAM IMPROVES THE PREDICTION OF DISEASE FREE SURVIVAL (DFS) FOR EARLY-STAGE LUNG CANCER PATIENTS", the contents of which are herein incorporated by reference in their entirety.

BACKGROUND

Lung cancer is one of the most significant cause of cancer related deaths in both men as well as women. Annually, there are approximately 228,820 new lung cancer cases and 135,720 estimated deaths in the United States alone. Broadly lung cancer can be divided into small cell and non-small cell lung cancer (NSCLC) where NSCLC accounts for almost 85% of total cases. Early stage accounts for stage IA to IIB diseases and significant proportion of these patients have recurrent disease even after curative resection.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Various embodiments discussed herein can build and/or employ a clinical-radiomics score for determining tumor prognoses based on a combination of radiomic features analyzed by a first machine learning model and pathomic features analyzed by a second machine learning model.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
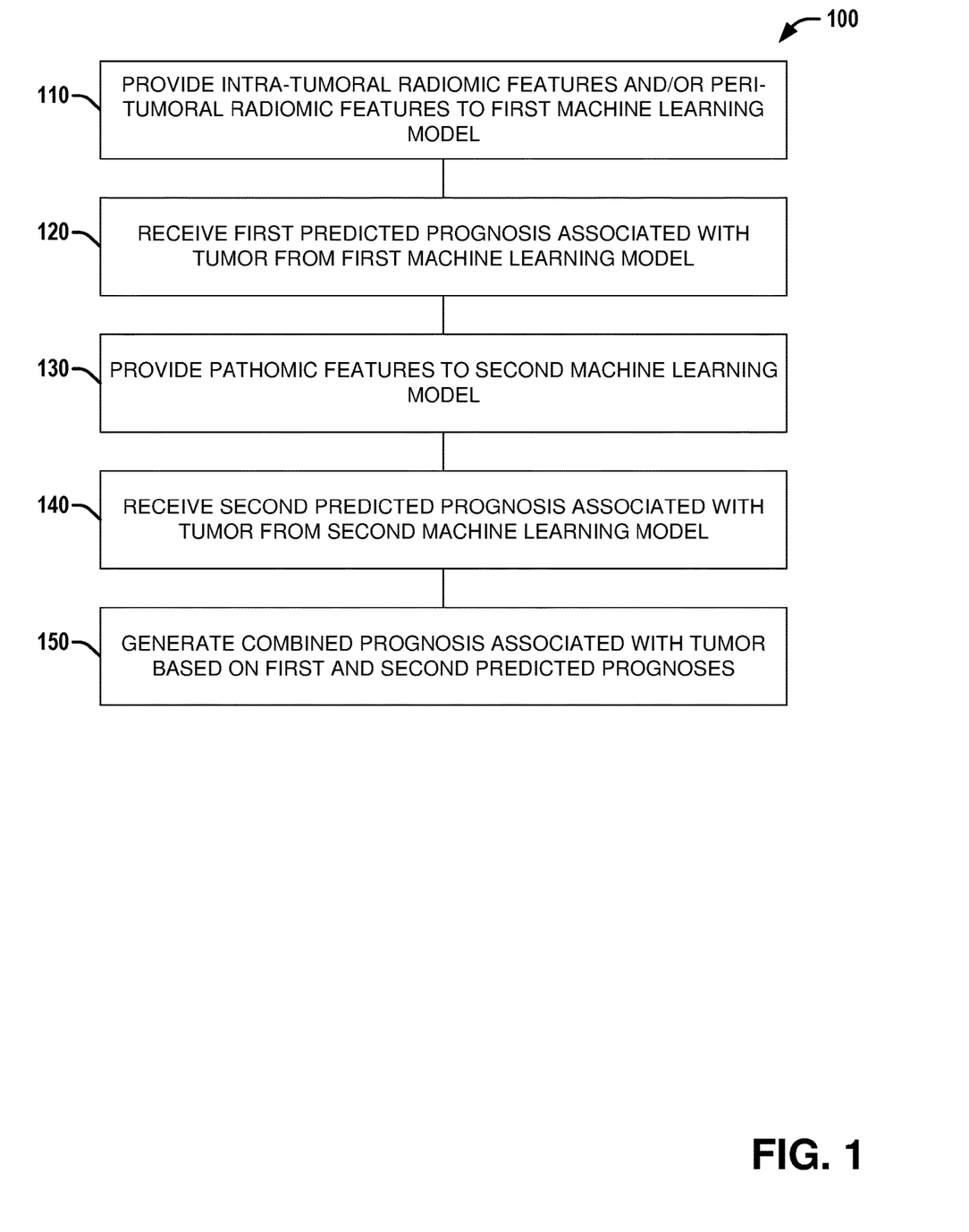
FIG. 1 illustrates a flow diagram of an example method/set of operations that can be performed by one or more processors to predict a prognosis for a tumor based on a combination of radiomic features analyzed by a first machine learning model and pathomic features analyzed by a second machine learning model, according to various embodiments discussed herein.

Referring to FIG. 1, illustrated is a flow diagram of an example method/set of operations 100 that can be performed by one or more processors to predict a prognosis for a tumor based on a combination of radiomic features analyzed by a first machine learning model and pathomic features analyzed by a second machine learning model, according to various embodiments discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, providing, to a first machine learning model, at least one of: one or more intra-tumoral radiomic features associated with a tumor or one or more peri-tumoral radiomic features associated with a peri-tumoral region around the tumor. In various embodiments, these radiomic features can be obtained separately from set of operations 100, or via accessing a medical imaging scan (e.g., MRI (contrast MRI, etc.), CT, etc.) of a tumor (e.g., segmented via expert annotation, computer segmentation (e.g., via deep learning, etc.), etc.), segmenting the tumor and/or peri-tumoral region, and extracting the radiomic features from the medical imaging scan. In various embodiments and in the example use case discussed below, the medical imaging scan can be obtained via a system and/or apparatus implementing the set of operations 100, or can be obtained from a separate medical imaging system (e.g., a MRI system/apparatus, a CT system/apparatus, etc.). Additionally, the medical imaging scan can be accessed contemporaneously with or at any point prior to performing the set of operations 100.

The set of operations 100 can further comprise, at 120, receiving a first predicted prognosis associated with the tumor from the first machine learning model.

The set of operations 100 can further comprise, at 130, providing, to a second machine learning model, one or more pathomic features associated with the tumor. In various embodiments, these pathomic features can be obtained separately from set of operations 100, or via accessing a digitized stained (e.g., H&E) histology image (e.g., a whole slide image or portion thereof) of a tumor, and extracting the radiomic features from the digitized histology image. In various embodiments and in the example use case discussed below, the digitized histology image can be obtained via a system and/or apparatus implementing the set of operations 100, or can be obtained from a separate imaging system (e.g., optical microscopy system/apparatus, etc.). Additionally, the digitized histology image can be accessed contemporaneously with or at any point prior to performing the set of operations 100.

The set of operations 100 can further comprise, at 140, receiving a second predicted prognosis associated with the tumor from the second machine learning model.

The set of operations 100 can further comprise, at 150, generating a combined prognosis (e.g., via an additional machine learning model, via a nomogram, etc.) associated with the tumor based on the first predicted prognosis and the second predicted prognosis.

Figure 2:
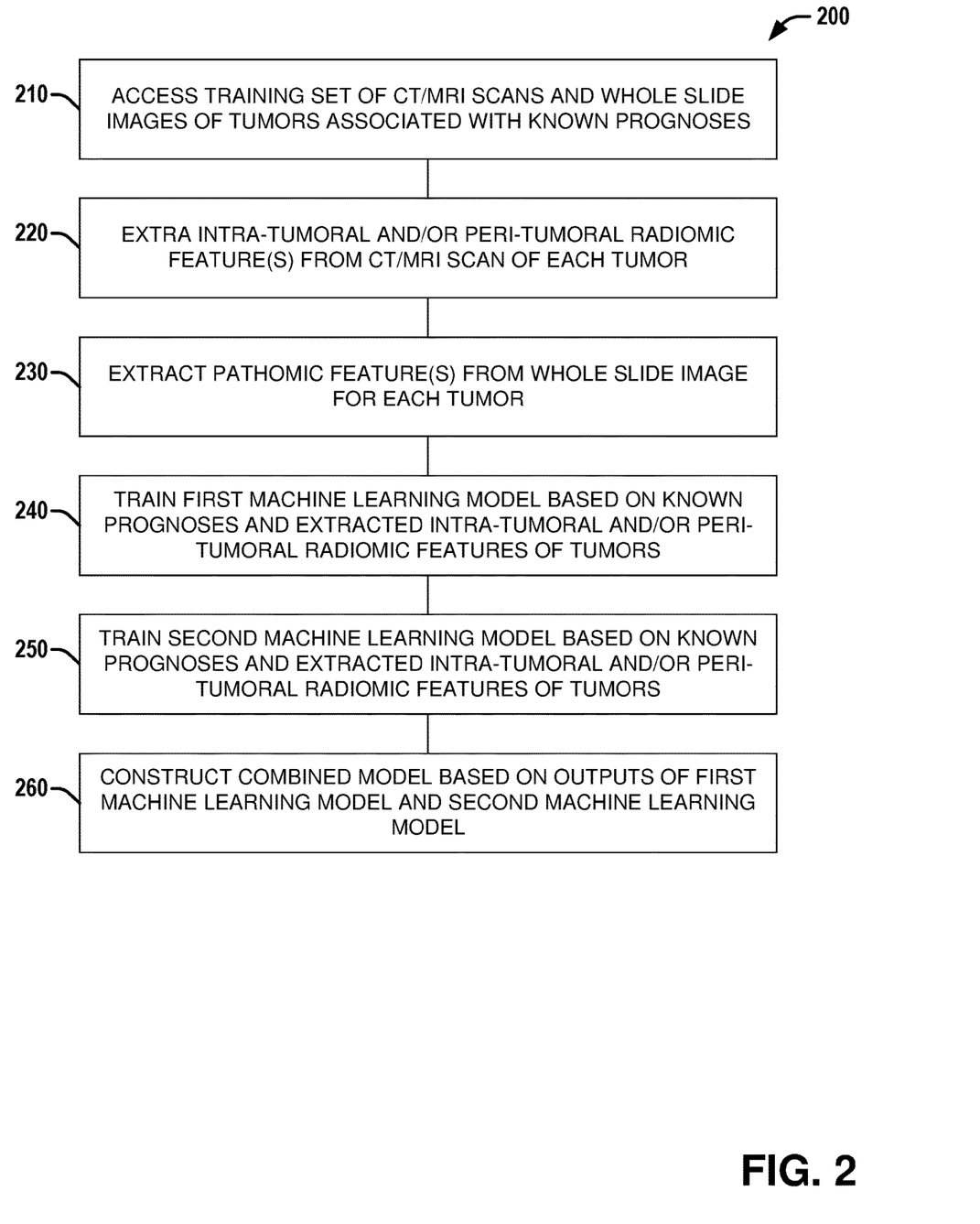
FIG. 2 illustrates a flow diagram of an example method/set of operations that can be performed by one or more processors to generate a model for determining a prognosis for a tumor based on a combination of radiomic features analyzed by a first machine learning model and pathomic features analyzed by a second machine learning model, according to various embodiments discussed herein.

Referring to FIG. 2, illustrated is a flow diagram of an example method/set of operations 200 that can be performed by one or more processors to generate a model for determining a prognosis for a tumor based on a combination of radiomic features analyzed by a first machine learning model and pathomic features analyzed by a second machine learning model, according to various embodiments discussed herein.

The set of operations 200 can comprise, at 210, accessing a training set comprising, for each tumor of a plurality of tumors, an associated medical imaging scan of that tumor and a digitized stained whole slide image (WSI) of that tumor, wherein each tumor of the plurality of tumors is associated with a known prognosis. In various embodiments and in the example use case discussed below, the training set can comprise medical imaging scans and/or histology scans (e.g., WSIs or portions thereof) that can be obtained via a system and/or apparatus implementing the set of operations 200, or can be obtained from separate medical imaging system(s). Additionally, the training set can be accessed contemporaneously with or at any point prior to performing the set of operations 200.

The set of operations 200 can further comprise, at 220, for each tumor of the plurality of tumors, extracting at least one of: one or more intra-tumoral radiomic features for that tumor from the associated medical imaging scan of that tumor and one or more peri-tumoral radiomic features for that tumor from a peri-tumoral region on the associated medical imaging scan of that tumor.

The set of operations 200 can further comprise, at 230, for each tumor of the plurality of tumors, extracting one or more pathomic features for that tumor from the digitized stained WSI of that tumor.

The set of operations 200 can further comprise, at 240, for each tumor of the plurality of tumors, training a first machine learning model, based on the known prognosis associated with that tumor and the at least one of the one or more intra-tumoral radiomic features for that tumor or the one or more peri-tumoral radiomic features for that tumor, to generate a first predicted prognosis for an additional tumor.

The set of operations 200 can further comprise, at 250, for each tumor of the plurality of tumors, training a second machine learning model, based on the known prognosis associated with that tumor and the one or more pathomic features for that tumor, to generate a second predicted prognosis for the additional tumor.

The set of operations 200 can further comprise, at 260, constructing a combined model configured to generate a combined prognosis for the additional tumor based on the first predicted prognosis and the second predicted prognosis. Additional aspects and embodiments are discussed below in connection with the following example use case.

Example Use Case: Combination of Radiomic and Pathomic Signature in the Nomogram Improves the Prediction of DFS for Early-Stage Lung Cancer Patients The following discussion provides example embodiments in connection with an example use case involving building and/or employing machine learning (ML)-based model(s) for predicting disease-free survival for early stage non-small cell lung cancer (ES-NSCLC) based on a combination of radiomic factors and pathomic factors.

Background: Early-Stage non-small cell lung cancer (ES-NSCLC) accounts for approximately 40% of NSCLC cases, with 5-year survival rates varying between 31-49%. Radiomic features can be extracted from baseline CT scans.

Methods: Retrospective chart review between 2005-14 yielded 70 ES-NSCLC patients from Cleveland clinic with available CT scans and H&E stained tissue slides. The CT scans were used for extracting a total of 248 intratumoral (IT) and peritumoral (PT) radiomic textural features. The H&E stained whole slides were used for extracting 242 pathomic features. The most stable, significant and uncorrelated features were selected from these two cohorts using LASSO cox models and radiomic and pathomic signatures were respectively constructed for predicting DFS. The two models were analyzed using hazard ratio (HR) and concordance index (CI). Nomogram and decision curve analysis was performed to analyze the individual and combined performance of two models.

Results: The top 6 radiomic features included features from the Haralick and collage families with 2 features from inside the nodule and 4 features from outside the tumor region. The Radiomic signature had a CI of 0.668 and HR of 2.4. The pathomic signature comprised 6 features from shape and graph based families and had 0.74 and 3.1 for CI and HR, respectively. The decision curve showed improved performance for predicting DFS after integrating the radiomic and pathomic signatures. The nomogram was constructed for the radiomic signature, pathomic signature and pathological stage, which improved the CI to 0.80, p<0.05.

Conclusion: The combination of Radiomic and Pathomic signature improves the prediction of DFS for the ES-NSCLC patients.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing machine learning models (e.g., unsupervised (e.g., clustering) or supervised (e.g., classifiers, etc.) models) to determine a prognosis (e.g., likelihood of disease-free survival) for a tumor based at least in part on features of medical imaging scans (e.g., MRI, CT, H&E stained WSI, etc.) that are not perceivable by the human eye, and involve computation that cannot be practically performed in the human mind. As one example, machine learning classifiers and/or deep learning models as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 3:
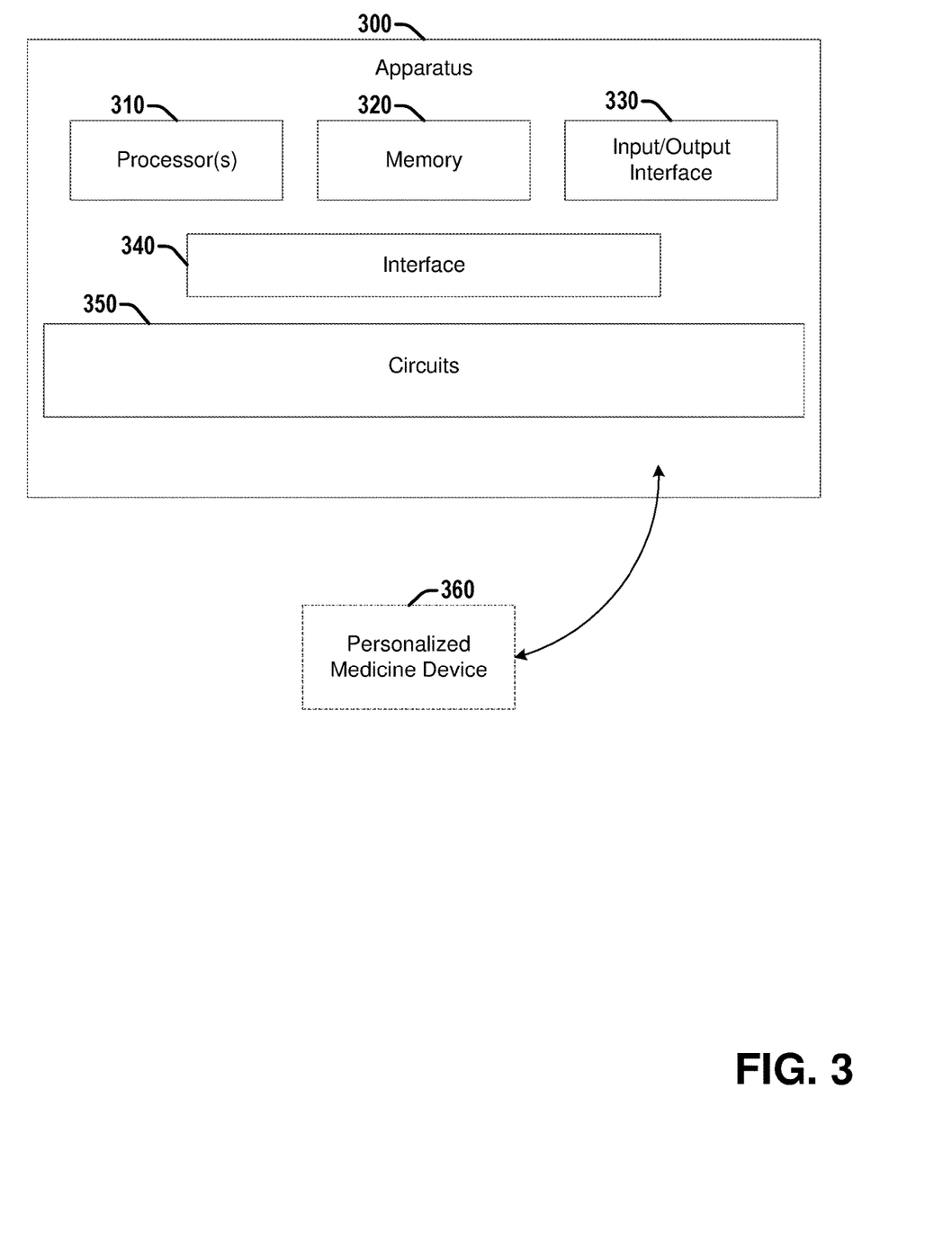
FIG. 3 illustrates a diagram of an example apparatus that can facilitate building and/or employing a clinical-radiomics score for determining tumor prognoses based on a combination of radiomic features analyzed by a first machine learning model and pathomic features analyzed by a second machine learning model, according to various embodiments discussed herein.

Referring to FIG. 3, illustrated is a diagram of an example apparatus 300 that can facilitate building and/or employing a clinical-radiomics score for determining tumor prognoses based on a combination of radiomic features analyzed by a first machine learning model and pathomic features analyzed by a second machine learning model, according to various embodiments discussed herein. Apparatus 300 can be configured to perform various techniques discussed herein, for example, various operations discussed in connection with sets of operations 100 and/or 200. Apparatus 300 can comprise one or more processors 310 and memory 320. Processor(s) 310 can, in various embodiments, comprise circuitry such as, but not limited to, one or more single-core or multi-core processors. Processor(s) 310 can include any combination of general-purpose processors and dedicated processors (e.g., graphics processors, application processors, etc.). The processor(s) can be coupled with and/or can comprise memory (e.g., of memory 320) or storage and can be configured to execute instructions stored in the memory 320 or storage to enable various apparatus, applications, or operating systems to perform operations and/or methods discussed herein. Memory 320 can be configured to store medical imaging scan(s) (e.g., CT, MRI, H&E stained WSI, etc.) Each of the medical imaging scan(s) can comprise a plurality of pixels or voxels, each pixel or voxel having an associated intensity. Memory 320 can be further configured to store additional data involved in performing operations discussed herein, such as radiomic and/or clinical features, or other information employed in various methods (e.g., 100, 200, etc.) discussed in greater detail herein.

Apparatus 300 can also comprise an input/output (I/O) interface 330 (e.g., associated with one or more I/O devices), a set of circuits 350, and an interface 340 that connects the processor(s) 310, the memory 320, the I/O interface 330, and the set of circuits 350. I/O interface 330 can be configured to transfer data between memory 320, processor 310, circuits 350, and external devices, for example, a medical imaging device (e.g., CT system, MRI system, optical microscopy system, etc.), and/or one or more remote devices for receiving inputs and/or providing outputs to a clinician, patient, etc., such as optional personalized medicine device 360.

The processor(s) 310 and/or one or more circuits of the set of circuits 350 can perform one or more acts associated with a method or set of operations discussed herein, such as set of operations 100 and/or 200. In various embodiments, different acts (e.g., different operations of a set of operations) can be performed by the same or different processor(s) 310 and/or one or more circuits of the set of circuits 350.

Apparatus 300 can optionally further comprise personalized medicine device 360. Apparatus 300 can be configured to provide a prognosis (e.g., prediction related to disease-free survival, etc.) for a patient determined based at least in part on a combination of pathomic features with intra-tumoral radiomic features and/or peri-tumoral radiomic features as discussed herein, and/or other data to personalized medicine device 360. Personalized medicine device 360 may be, for example, a computer assisted diagnosis (CADx) system or other type of personalized medicine device that can be used to facilitate monitoring and/or treatment of an associated medical condition. In some embodiments, processor(s) 310 and/or one or more circuits of the set of circuits 350 can be further configured to control personalized medicine device 360 to display the prognosis for a clinician or the patient or other data on a computer monitor, a smartphone display, a tablet display, or other displays.

Examples herein can include subject matter such as an apparatus, a medical image system/apparatus, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: providing, to a first machine learning model, at least one of: one or more intra-tumoral radiomic features associated with a tumor or one or more peri-tumoral radiomic features associated with a peri-tumoral region around the tumor; receiving a first predicted prognosis associated with the tumor from the first machine learning model; providing, to a second machine learning model, one or more pathomic features associated with the tumor; receiving a second predicted prognosis associated with the tumor from the second machine learning model; and generating a combined prognosis associated with the tumor based on the first predicted prognosis and the second predicted prognosis.

Example 2 comprises the subject matter of any variation of any of example(s) 1, wherein the combined prognosis is one of disease-free survival (DFS), non-DFS, or a likelihood of DFS.

Example 3 comprises the subject matter of any variation of any of example(s) 1-2, wherein at least one of the one or more intra-tumoral radiomic features or the one or more peri-tumoral radiomic features comprise a first-order statistic of one or more of the following, extracted from the one of the medical imaging scan or the medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLlAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

Example 4 comprises the subject matter of any variation of any of example(s) 3, wherein the first-order statistic is one of a mean, a median, a standard deviation, a skewness, a kurtosis, a range, a minimum, a maximum, a percentile, or histogram frequencies.

Example 5 comprises the subject matter of any variation of any of example(s) 1-4, wherein the peri-tumoral region comprises an annular region around the tumor.

Example 6 comprises the subject matter of any variation of any of example(s) 1-5, wherein the tumor is an early-stage non-small cell lung cancer (ES-NSCLC) tumor.

Example 7 comprises the subject matter of any variation of any of example(s) 1-6, wherein at least one of the first machine learning model or the second machine learning model is one of, or an ensemble of two or more of: a least absolute shrinkage and selection operator (Lasso)-regularized multivariate Cox-regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, a LASSO model, an elastic net, a Gaussian process classification, or a nearest neighbors classification.

Example 8 comprises the subject matter of any variation of any of example(s) 1-7, wherein the one or more pathomic features comprise at least one of: a shape feature, a texture feature, or a graph feature.

Example 9 comprises the subject matter of any variation of any of example(s) 1-8, wherein the instructions further comprise: accessing a medical imaging scan of the tumor, wherein the medical imaging scan is one of a computed tomography (CT) scan or a magnetic resonance imaging (MRI) scan; segmenting a peri-tumoral region around the tumor; and extracting the at least one of the one or more intra-tumoral radiomic features from the tumor or the one or more peri-tumoral radiomic features from the peri-tumoral region.

Example 10 comprises the subject matter of any variation of any of example(s) 1-9, wherein the instructions further comprise: accessing a digitized stained whole slide image (WSI) of the tumor; and extracting the one or more pathomic features from the digitized WSI.

Example 11 is an apparatus, comprising: a memory configured to store one or more pathomic features associated with a tumor, and at least one of: one or more intra-tumoral radiomic features associated with the tumor or one or more peri-tumoral radiomic features associated with a peri-tumoral region around the tumor; and one or more processors configured to: provide, to a first machine learning model, the at least one of the one or more intra-tumoral radiomic features associated with a tumor or the one or more peri-tumoral radiomic features associated with a peri-tumoral region around the tumor; receive a first predicted prognosis associated with the tumor from the first machine learning model; provide, to a second machine learning model, the one or more pathomic features associated with the tumor; receive a second predicted prognosis associated with the tumor from the second machine learning model; and generate a combined prognosis associated with the tumor based on the first predicted prognosis and the second predicted prognosis.

Example 12 comprises the subject matter of any variation of any of example(s) 11, wherein the combined prognosis is one of disease-free survival (DFS), non-DFS, or a likelihood of DFS.

Example 13 comprises the subject matter of any variation of any of example(s) 11-12, wherein at least one of the one or more intra-tumoral radiomic features or the one or more peri-tumoral radiomic features comprise a first-order statistic of one or more of the following, extracted from the one of the medical imaging scan or the medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLlAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

Example 14 comprises the subject matter of any variation of any of example(s) 13, wherein the first-order statistic is one of a mean, a median, a standard deviation, a skewness, a kurtosis, a range, a minimum, a maximum, a percentile, or histogram frequencies.

Example 15 comprises the subject matter of any variation of any of example(s) 11-14, wherein the peri-tumoral region comprises an annular region around the tumor.

Example 16 comprises the subject matter of any variation of any of example(s) 11-15, wherein the tumor is an early-stage non-small cell lung cancer (ES-NSCLC) tumor.

Example 17 comprises the subject matter of any variation of any of example(s) 11-16, wherein at least one of the first machine learning model or the second machine learning model is one of, or an ensemble of two or more of: a least absolute shrinkage and selection operator (Lasso)-regularized multivariate Cox-regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, a LASSO model, an elastic net, a Gaussian process classification, or a nearest neighbors classification.

Example 18 comprises the subject matter of any variation of any of example(s) 11-17, wherein the one or more pathomic features comprise at least one of: a shape feature, a texture feature, or a graph feature.

Example 19 is a non-transitory computer-readable medium storing computer-executable instructions that, when executed, cause a processor to perform operations, comprising: accessing a training set comprising, for each tumor of a plurality of tumors, an associated medical imaging scan of that tumor and a digitized stained whole slide image (WSI) of that tumor, wherein each tumor of the plurality of tumors is associated with a known prognosis; for each tumor of the plurality of tumors: extracting at least one of: one or more intra-tumoral radiomic features for that tumor from the associated medical imaging scan of that tumor and one or more peri-tumoral radiomic features for that tumor from a peri-tumoral region on the associated medical imaging scan of that tumor; extracting one or more pathomic features for that tumor from the digitized stained WSI of that tumor; training a first machine learning model, based on the known prognosis associated with that tumor and the at least one of the one or more intra-tumoral radiomic features for that tumor or the one or more peri-tumoral radiomic features for that tumor, to generate a first predicted prognosis for an additional tumor; and training a second machine learning model, based on the known prognosis associated with that tumor and the one or more pathomic features for that tumor, to generate a second predicted prognosis for the additional tumor; and constructing a combined model configured to generate a combined prognosis for the additional tumor based on the first predicted prognosis and the second predicted prognosis.

Example 20 comprises the subject matter of any variation of any of example(s) 19, wherein the prognosis is one of disease-free survival (DFS), non-DFS, or a likelihood of DFS, and wherein each tumor of the plurality of tumors is an early-stage non-small cell lung cancer (ES-NSCLC) tumor.

Example 21 comprises the subject matter of any variation of any of example(s) 19, wherein at least one of the one or more intra-tumoral radiomic features or the peri-tumoral radiomic features comprise a first-order statistic of one or more of the following, extracted from one of that medical imaging scan or that medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLIAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

Example 22 comprises the subject matter of any variation of any of example(s) 19, wherein the combined model comprises a nomogram.

Example 23 comprises an apparatus comprising means for executing any of the described operations of examples 1-22.

Example 24 comprises a machine readable medium that stores instructions for execution by a processor to perform any of the described operations of examples 1-22.

Example 25 comprises an apparatus comprising: a memory; and one or more processors configured to: perform any of the described operations of examples 1-22.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
   inputting, to a first machine learning model: one or more intra-tumoral radiomic features associated with a tumor and one or more peri-tumoral radiomic features associated with a peri-tumoral region around the tumor, wherein the one or more intra-tumoral radiomic features and the one or more peri-tumoral radiomic features comprise at least one texture feature;
   receiving a first predicted prognosis associated with the tumor from the first machine learning model;
   inputting, to a second machine learning model, one or more pathomic features associated with the tumor, wherein the one or more pathomic features comprise at least one spatial feature;
   receiving a second predicted prognosis associated with the tumor from the second machine learning model; and
   generating a combined prognosis associated with the tumor using the first predicted prognosis and the second predicted prognosis as inputs into a model.

2. The non-transitory computer-readable medium of claim 1, wherein the combined prognosis is one of disease-free survival (DFS), non-DFS, or a likelihood of DFS.

3. The non-transitory computer-readable medium of claim 1, wherein the at least one texture feature comprises at least one Haralick feature and at least one Co-occurrence of Local Anisotropic Gradient Orientations (CoLIAGe) feature.

4. The non-transitory computer-readable medium of claim 3,
   wherein the at least one texture feature comprises a first-order statistic of the at least one Haralick feature and the at least one CoLIAGe feature; and
   wherein the first-order statistic is one of a mean, a median, a standard deviation, a skewness, a kurtosis, a range, a minimum, a maximum, a percentile, or histogram frequencies.

5. The non-transitory computer-readable medium of claim 1, wherein the peri-tumoral region comprises an annular region around the tumor.

6. The non-transitory computer-readable medium of claim 1, wherein the tumor is an early-stage non-small cell lung cancer (ES-NSCLC) tumor.

7. The non-transitory computer-readable medium of claim 1, wherein at least one of the first machine learning model or the second machine learning model is one of, or an ensemble of two or more of: a least absolute shrinkage and selection operator (Lasso)-regularized multivariate Cox-regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, a LASSO model, an elastic net, a Gaussian process classification, or a nearest neighbors classification.

8. The non-transitory computer-readable medium of claim 1, wherein the at least one spatial feature comprises a shape feature and a graph feature.

9. The non-transitory computer-readable medium of claim 1, wherein the operations further comprise:
   accessing a medical imaging scan of the tumor, wherein the medical imaging scan is one of a computed tomography (CT) scan or a magnetic resonance imaging (MRI) scan;
   segmenting the peri-tumoral region around the tumor; and
   extracting the at least one of the one or more intra-tumoral radiomic features from the tumor or the one or more peri-tumoral radiomic features from the peri-tumoral region.

10. The non-transitory computer-readable medium of claim 1, wherein the operations further comprise:
    accessing a digitized stained whole slide image (WSI) of the tumor; and
    extracting the one or more pathomic features from the digitized WSI.

11. An apparatus, comprising:
    a memory configured to store one or more pathomic features associated with a tumor, and: one or more intra-tumoral radiomic features associated with the tumor and one or more peri-tumoral radiomic features associated with a peri-tumoral region around the tumor, wherein the one or more intra-tumoral radiomic features and the one or more peri-tumoral radiomic features comprise at least one texture feature, and wherein the one or more pathomic features comprise at least one spatial feature; and
    one or more processors configured to:
      input, to a first machine learning model, the at least one of the one or more intra-tumoral radiomic features associated with the tumor and the one or more peri-tumoral radiomic features associated with the peri-tumoral region around the tumor;
      receive a first predicted prognosis associated with the tumor from the first machine learning model;
      input, to a second machine learning model, the one or more pathomic features associated with the tumor;
      receive a second predicted prognosis associated with the tumor from the second machine learning model; and
      generate a combined prognosis associated with the tumor using the first predicted prognosis and the second predicted prognosis as inputs into a model.

12. The apparatus of claim 11, wherein the combined prognosis is one of disease-free survival (DFS), non-DFS, or a likelihood of DFS.

13. The apparatus of claim 11, wherein the at least one texture feature comprises at least one Haralick feature and at least one Co-occurrence of Local Anisotropic Gradient Orientations (CoLIAGe) feature.

14. The apparatus of claim 13,
wherein the at least one texture feature comprises a first-order statistic of the at least one Haralick feature and the at least one CoLIAGe feature; and
wherein the first-order statistic is one of a mean, a median, a standard deviation, a skewness, a kurtosis, a range, a minimum, a maximum, a percentile, or histogram frequencies.

15. The apparatus of claim 11, wherein the peri-tumoral region comprises an annular region around the tumor.

16. The apparatus of claim 11, wherein the tumor is an early-stage non-small cell lung cancer (ES-NSCLC) tumor.

17. The apparatus of claim 11, wherein at least one of the first machine learning model or the second machine learning model is one of, or an ensemble of two or more of: a least absolute shrinkage and selection operator (Lasso)-regularized multivariate Cox-regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, a LASSO model, an elastic net, a Gaussian process classification, or a nearest neighbors classification.

18. The apparatus of claim 11, wherein the at least one spatial feature comprises a shape feature and a graph feature.

19. A non-transitory computer-readable medium storing computer-executable instructions that, when executed, cause a processor to perform operations, comprising:
accessing a training set comprising, for each tumor of a plurality of tumors, an associated medical imaging scan of that tumor and a digitized stained whole slide image (WSI) of that tumor, wherein each tumor of the plurality of tumors is associated with a known prognosis;
for each tumor of the plurality of tumors:
extracting at least one of: one or more intra-tumoral radiomic features for that tumor from the associated medical imaging scan of that tumor and one or more peri-tumoral radiomic features for that tumor from a peri-tumoral region on the associated medical imaging scan of that tumor;
extracting one or more pathomic features for that tumor from the digitized stained WSI of that tumor;
training a first machine learning model, based on the known prognosis associated with that tumor and the at least one of the one or more intra-tumoral radiomic features for that tumor or the one or more peri-tumoral radiomic features for that tumor, to generate a first predicted prognosis for an additional tumor; and
training a second machine learning model, based on the known prognosis associated with that tumor and the one or more pathomic features for that tumor, to generate a second predicted prognosis for the additional tumor; and constructing a combined model configured to generate a combined prognosis for the additional tumor using the first predicted prognosis and the second predicted prognosis as inputs to the combined model.

20. The non-transitory computer-readable medium of claim 19, wherein the combined prognosis is one of disease-free survival (DFS), non-DFS, or a likelihood of DFS, and wherein each tumor of the plurality of tumors is an early-stage non-small cell lung cancer (ES-NSCLC) tumor.

21. The non-transitory computer-readable medium of claim 19, wherein at least one of the one or more intra-tumoral radiomic features or the peri-tumoral radiomic features comprise a first-order statistic of one or more of the following, extracted from one of the associated medical imaging scan or a medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLIAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

22. The non-transitory computer-readable medium of claim 19, wherein the combined model comprises a nomogram.

23. An apparatus, comprising one or more processors configured to:
compute one or more first features from a first image associated with a first image modality, wherein the first image depicts a tissue pathology;
compute one or more second features from a second image associated with a second image modality, wherein the second image depicts the tissue pathology; and
generate a combined prediction of the tissue pathology's pathologic or phenotypic state using the one or more first features and the one or more second features as inputs to a model.

24. The apparatus of claim 23, wherein the first image modality is radiology image data, the second image modality is tissue slide image data, and the one or more first features and the one or more second features are computed based upon the tissue pathology or tissue surrounding the tissue pathology.

25. The apparatus of claim 23, wherein the first image modality is radiology image data, wherein the one or more processors are further configured to compute the one or more first features based solely on the radiology image data.

26. The apparatus of claim 23, wherein the second image modality is tissue slide image data, wherein the one or more processors are further configured to compute the one or more second features based solely on the tissue slide image data.

27. The apparatus of claim 23, wherein the one or more processors are further configured to compute the one or more first features and the one or more second features using a neural network.

* * * * *